(12) United States Patent
Lin et al.

(10) Patent No.: US 6,458,292 B1
(45) Date of Patent: Oct. 1, 2002

(54) COMPOSITION OF AN ANTI-SCALE-FORMING AGENT

(75) Inventors: Jiang-Jen Lin, Taichung; Jann-Chen Lin; Wen-Hen Lô, both of Chiayi; Wen-Shwong Hwang, Yunlin; Kun-Hai Lin, Chiayi, all of (TW)

(73) Assignee: Chinese Petroleum Corp., Taipei (TW)

( * ) Notice: Subject to any disclaimer, the term of this patent is extended or adjusted under 35 U.S.C. 154(b) by 0 days.

(21) Appl. No.: 09/686,937

(22) Filed: Oct. 12, 2000

(51) Int. Cl.[7] .............................. C02F 5/14; C10G 9/12; C10G 9/16; C07F 9/44
(52) U.S. Cl. ............. 252/180; 252/188.28; 252/400.22; 564/14; 564/12; 208/48 R; 208/48 AA; 585/950
(58) Field of Search .......................... 252/180, 188.28, 252/188.1, 400.22; 508/228, 427; 564/14, 12; 210/666, 668; 208/47, 48 R, 48 AA; 585/950; 525/180

(56) References Cited

U.S. PATENT DOCUMENTS

| | | | | |
|---|---|---|---|---|
| 3,261,774 A | * | 7/1966 | Newkirk et al. | ........ 208/48 AA |
| 3,538,080 A | * | 11/1970 | Ham | .......................... 525/340 |
| 3,940,345 A | * | 2/1976 | Caunt | .......................... 502/114 |
| 5,360,531 A | * | 11/1994 | Tong et al. | ................ 208/48 R |

OTHER PUBLICATIONS

McGraw–Hill Dictionary of Chemical terms, Edited by Sybil Parker, (McGraw–Hill Book Co., NY, NY, copyright 1984), p. 337 (Dec. 1987).*

* cited by examiner

*Primary Examiner*—Daniel S. Metzmaier
(74) *Attorney, Agent, or Firm*—Bacon & Thomas

(57) ABSTRACT

A composition for an anti-scale-forming agent includes oil-based polyalkylenes, amines phosphorous and oxygen in a polymer for providing dispersivity and anti-oxidation and having the following formula:

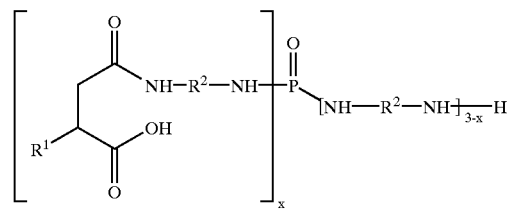

By integrating both characteristics into a single polymer, the anti-scale-forming agent in accordance with the present invention can be used as an anti-scale-forming agent for a manufacturing process in a petroleum refinery plant or the like chemistry factory. $R^1$, $R^2$ and x are defined herein.

7 Claims, 3 Drawing Sheets

COMPOSITION OF AN ANTI-SCALE-FORMING AGENT

BACKGROUND OF THE INVENTION

(1) Field of the Invention

The invention relates to a composition of an anti-scale-forming agent for dispersing scales and for anti-oxidation, and more particularly to an additive which can be added during a chemical process of a heat-exchanger, a reactor, a distillation tower or the like in a power plant, a petroleum refinery or the like chemistry plant.

(2) Description of the Prior Art

An anti-scale-forming agent is one of typical chemicals that are widely used in petroleum-related and petroleum-refinery industry. Generally, in an intern process of the industry including an oil-cracking process, a reforming process or a de-ethylene process, the reaction temperature may be as high as 200~500° C. Meanwhile, hydrocarbons in a reaction chamber will be deformed through oxidation or polymerization to generate scales. The scales accumulated in the piping and the furnace wall may affect the processing flow, more even block the valves and piping, and lower the heat-transfer efficiency. As a result, energy is wasted and production will be inevitably reduced due to frequently shutdown for cleaning the scales in the piping. Therefore, usage of anti-scale-forming agent in a chemistry plant is important and frequently seen.

The forming of scales is one of general chemistry phenomena. The scale is a gel-form or carbonic-acid coke product that is cracked from a polymer, in which the polymer is formed from a reaction mechanism of free radicals through oxidation upon impurities or the hydrocarbon itself. In addition, in the case that the impurities include metal substance such as Cu or Fe, the forming of free radicals will be accelerated and thus the forming of scales will be serious. Therefore, the anti-scale-forming agent is usually made to be a good anti-oxidizer or a metal de-activator. Actually, there are already several kinds of the anti-scale-forming agents in the market to meet various applications in the industry; such as the U.S. Pat. No. 4,775,495 disclosing a control method upon oxidation for a petroleum-related process, and the U.S. Pat. No. 5,211,836 introducing anti-oxidants and an interface-dispersing theory for various process to enhance economic efficiency.

SUMMARY OF THE INVENTION

Accordingly, it is a primary object of the present invention to provide a composition for an anti-scale-forming agent that can disperse the scales and prevent from the oxidization. The scale-dispersivity of the agent is obtained through a dispersing theory for a hydrophilic/oil-philic balanced interface agent in a molecular formula. By integrating the dispersivity and the anti-oxidization in a single polymer, the excellent anti-scale-forming agent of the present invention can be formed and can be applied to the petroleum-refinery and other chemistry processes for providing effects of anti-oxidizing and anti-scale-forming.

To achieve aforesaid purposes, the composition of the anti-scale-forming agent in accordance with the present invention includes polyalkylenes, amines phosphorous and oxygen in a polymer for providing substantial dispersivity and anti-oxidization. The chemical formula of the polymer can be expressed as:

$$(R^1R^2)_xPOR^2_{3-x}$$

in which $R^1$ and $R^2$ are selected from polyalkylenes, poly etheramines or polyamines having oxyakLenes. In the expression, O is oxygen, P is phosphorous, and x is 1 or 2.

In application, aforesaid formula $(R^1R^2)_xPOR^2_{3-x}$ can be chemically structured as follows.

(A)

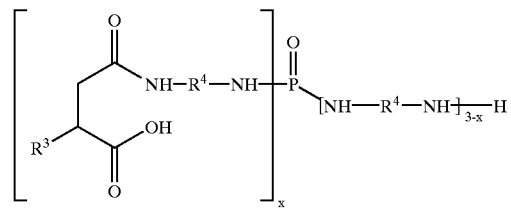

$R^3$=alkyl, e.g. polyisobutyleneyl (PIB)

In addition, the structure shown above can be obtained through the following reaction.

x=1 or 2

(A) is made by the following formula:

(B)

$$H_2N-R^4-NH_2 + POCl_3 \longrightarrow \underset{\underset{O}{\|}}{-P}-(NH-R^2-NH_2)_3$$

(B)+polyisobutylenesuccinic anhydride (PIBSA) $\xrightarrow{\text{DifferentMoleRatio}}$ (A)

Select one of polyalkylenes formed by alkylenes through a polymerization reaction. The polyalkylene is then used to derive an acid-anhydride, and the acid-anhydride is further used to form an additive product through reaction with oxygen and phosphorous containing amine. The additive product has a high oil-resolvability, and at least two amines for bonding effect, and phosphide for anti-oxidizing. The additive product as the anti-scale-forming agent according to the present invention can integrate at least two characteristics into a single polymer so that it can contribute greatly to the oil-refinery factories and other chemistry factories.

All these objects are achieved by the composition of the anti-scale-forming agent described below.

BRIEF DESCRIPTION OF THE DRAWINGS

The present invention will now be specified with reference to its preferred embodiment illustrated in the drawings, in which.

DESCRIPTION OF THE PREFERRED EMBODIMENT

The invention disclosed herein is directed to a composition of an anti-scale-forming agent. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

According to the present invention, an anti-scale-forming agent with excellent anti-oxidization and anti-scale-formation is provided to integrate oil-based polyalkylenes, amines phosphorous oxygen amines in a polymer. The anti-oxidization provided by the polyalkylenes with phosphors and the bonding capability provided by the amines with aminos enable the polymer of the present invention to have the scale-dispersivity and the anti-oxidization at the same time.

In the present invention, the polyalkylenes can be derived from oil-based polyalkylenes through polymerization upon alkylenes. The polyalkylene can have a molecular weight of above 600, preferably ranged between 600 and 1500. In the present invention, the amine can be one of polyetheramines or poly oxyalkylene amines which includes at least an organic function. Suitable polyamines for the present invention can be selected from the following chemicals.

a. $N_2HCH_2CH_2NH_2$ (ethylene diamine, EDA)',
b. $H_2N(CH_2)5NH2$ (1,6-diamino hexane)',
c. $H_2N(CH_2)_2NH(CH_2)_2NH_2$ (diethylenetriamine, DETA)',
d. $H_2NC(CH_3)HCH_2$ $(OCH_2C(CH_3)H)_xNH_2$ (x=2~3, D-230)',
e. $H_2N(CH_2)_2NH(CH_2)_2NH(CH_2)_2NH_2$ (triethyleneteramine, TETA)',
f. $(CH_3CH_2)_2N(CH_2)_3NH_3(N, N$-diethyl-1,3-propane diamine)',
g. $H_2N(HC(CH_3)H_2CO)_xH_2C_2$-$(CH_2$—$(OCH_2C(CH_3)H)$ X—$NH_2)_2C_2H_5$,
h. $H_2N(CH_2CH_2O)_2CH_2CH_2NH_2$,
i. $(CH_3)_2N(CH_2)_3NH_2$ (N, N-dimethyl-1, 3-propane diamine)

The amine above might have a molecular weight of above 200, preferably ranged between 200 and 2000.

Figure 1:
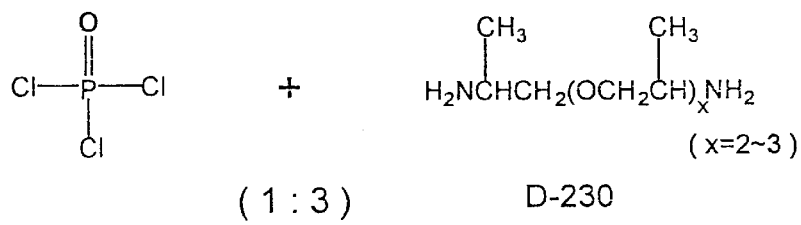
FIG. 1 is a schematic view of a chemistry equation and a reaction for a first embodiment of the anti-scale-forming agent in accordance with the present invention.
Figure 1:
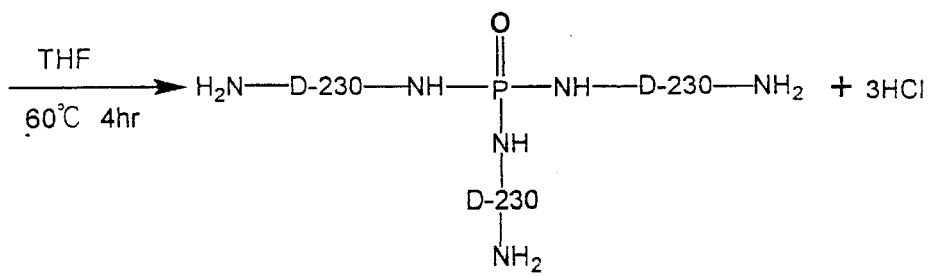
Figure 1:
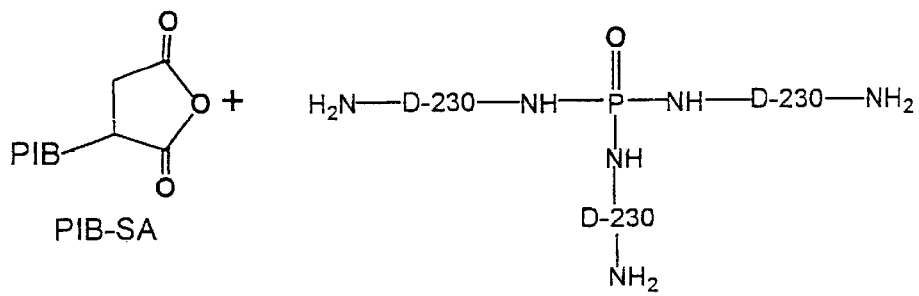
Figure 1:
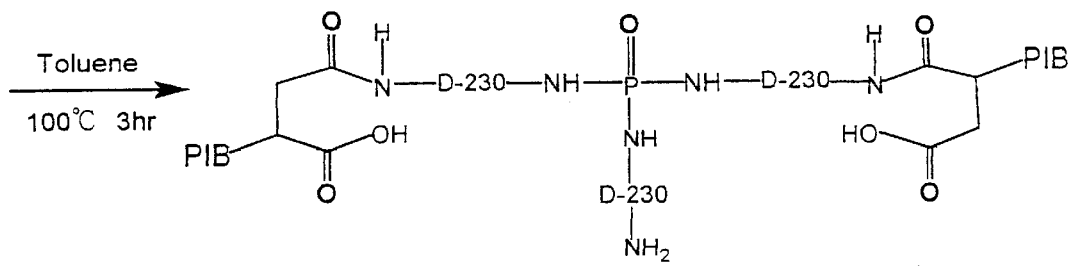
Figure 1:
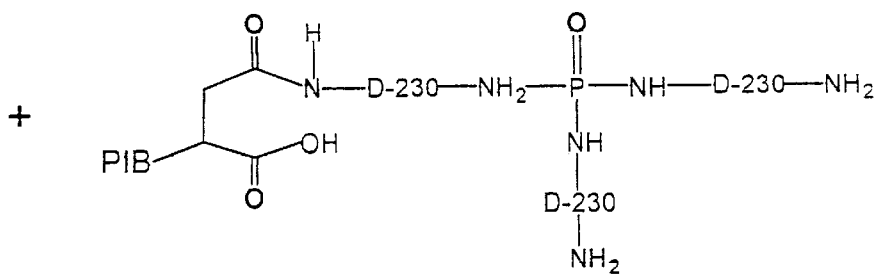

In the present invention, the anti-scale-forming agent can have a preferred chemistry structure as follows.

through a polymerization. The PIB is then used to form a PIB-SA with a molecular weight of 300 to 2000. Finally, the coupler and the PIB-SA are reacted to derive the final product, the anti-scale-forming agent of the present invention as shown in FIG. 1.

The novel anti-scale-forming agent of the present invention can be applied to any heat exchanger, reactor, or distillation tower in a power plant or a chemistry factory. Moreover, the ASTM D3241 testing can be used to verify the agent. According to the present invention, it is foreseeable that various anti-scale-forming agents of the same kind can be derived to meet specific factory processes.

Effects and various advantages by applying the present invention will be further described through the preferred embodiment and the related testing procedures raised below.

EMBODIMENT

Use double amount of TBF respectively to dissolve $POCl_3$ (5.4 g, 0.035 mole) and polyetherdiamine (24.15 g, 0.105 mole). Under the room temperature, titrate the $POCl_3$ into the polyetherdiamine and will dissipate above 10° C. heat. Heat the solution to 60° C. and keep 4 hours for reaction. Then, lower the solution to the room temperature and rid off the THF by lowering the pressure and increasing the concentration. Dissolve one concentrated sample by $CHCl_3$, neutrally react the sample solution with an $NaHCO_3$ solution to derive a middle product HCl, and then extract a layer of organics. After a pressure-lowering and concentration process to rid off $CHCl_3$, a middle product named B1 is obtained. Bring PIB-SA (11.02 g, 0.00992 mole) into a tri-neck bottle, and add in B1 (4.8532 g, 0.00612 mole) and overdose Toluene as the solvent. Have the PIB-SA solution heated and stirred to 100° C. and kept 4 hours for reaction. Then, after a pressure lowering and concentration process, the Toluene is removed and a final product can be obtained for a further FT-IR testing. Under a reaction temperature of 60° C. for the FT-IR testing, a specimen of the final product is verified to have O=P—N—H fue to the existence of three absorption peaks at 1020.4 cm$^{-1}$, 907.1 cm$^{-1}$ and 1592.2 cm$^{-1}$. In a second procedure of 100° C. reaction temperature, the specimen of the final product is verified to have amic acids due to the existence of two absorption peaks at 1641.9 cm$^{-1}$ and 1545.3 cm$^{-1}$ (weak). The completion of the reaction can be ascertained by observing the disappear-

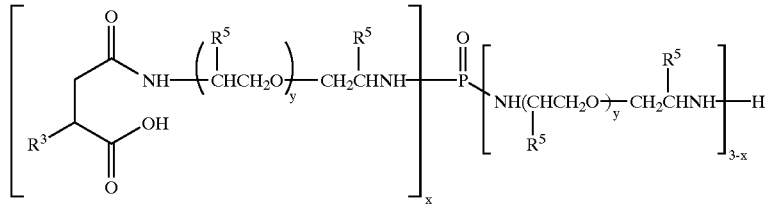

$R^3$=PIB
$R^5$=H, $CH_3$ or $C_2H_5$
x=1 or 2
y=1~20

In the above formula, poly oxyalkylene amines, PIB and the phosphides are coexistent.

One suitable forming method for producing the anti-scale-forming agent of the present invention can include a step of forming a coupler by coupling $POCl_3$ and polyetheramine by ridding off HCl. On the other hand, isobutylene can be used to derive a PIB with a molecular weight of 800 to 2000, ance of two IR absorption peaks for the specimen at 1786.0 cm$^{-1}$ (strong) and 1862.2 cm$^{-1}$ (weak).

In the following testing processes, analytic characteristics of the anti-oxidization agent in the preferred embodiment of the present invention will be revealed. In the following description, ΔT for adding the anti-oxidization agent is according to the ASTM D3241 testing specs.

Table 1 shows various compositions of anti-scale-forming agents, formed under 80° C. The anti-oxidization effect of the agents in 3 hours according to the ASTM D3241 and the titration value for the first, the second and the third degrees, amines are also shown. In the table, both POCl₃ and DCP have the phosphor. Polyetherdiamine (D-230 shown in FIG. 1) and phenylene diamine have the amino. It is found, by comparing A1 with A3 or by comparing A4 with A4, that the composition having the D-230 can reveal the characteristics of the first and the second degree amines, and thus can present better bonding effect. It is also found, by comparing A1 with A3, that ΔT for the agent with the D-230 is higher than that for those with the phenylene diamine. Therefore, the A1 with the D-230 can present better anti-oxidization capability.

Figure 2:
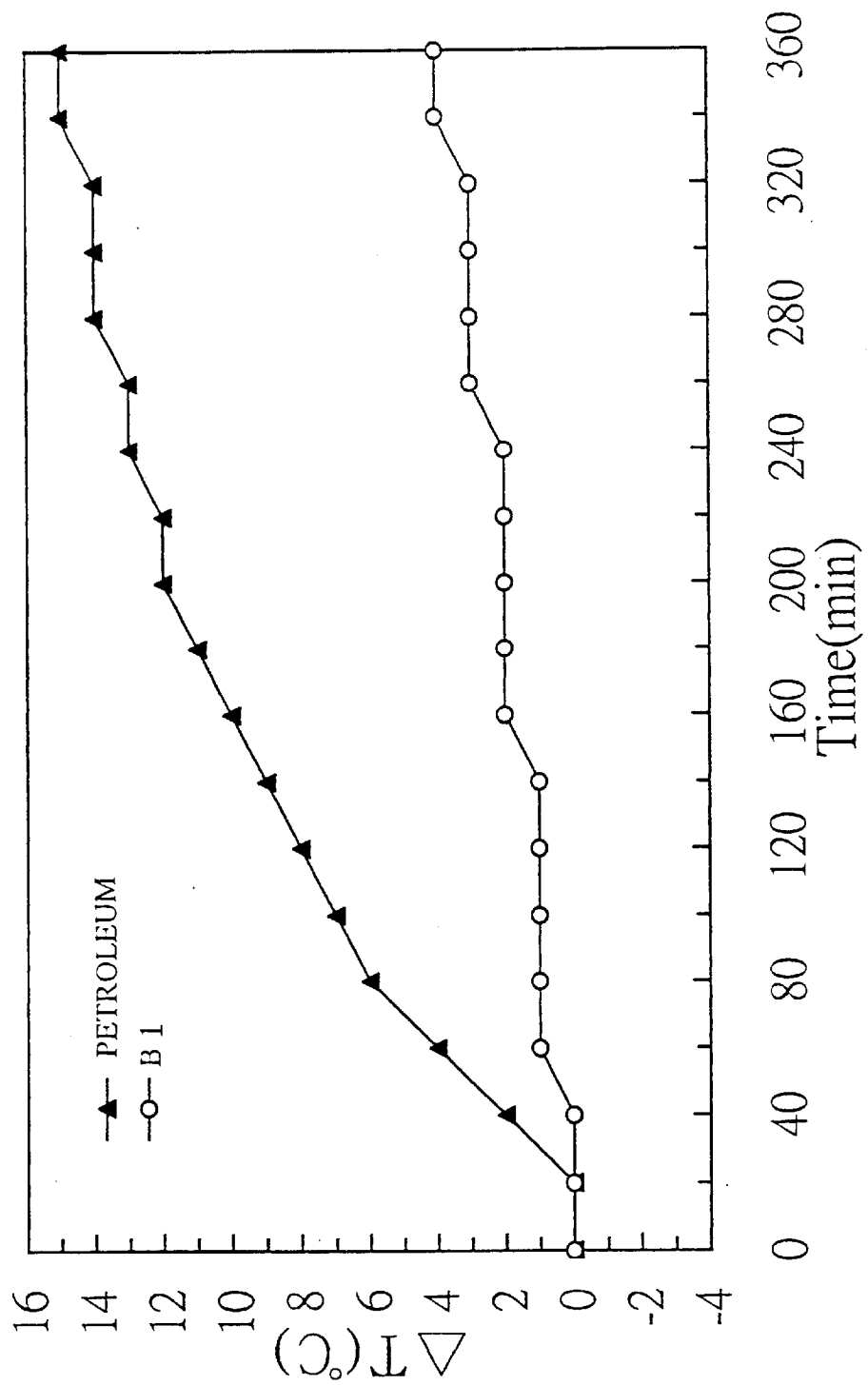
FIG. 2 is an ASTM D3241 testing plot by adding the anti-scale-forming agent of the present invention.

FIG. 2 is an ASTM D3241 testing plot by adding the anti-scale-forming agent of the present invention. The testing pressure and temperature are 500 psi and 371° C., respectively. The 150-ppm anti-oxidization agent is added by a flow rate of 1.5 cc/min. From FIG. 2, it is found that, during a petroleum refinery process, ΔT of the testing will increase as the reaction time. After adding the anti-oxidization agent B1, ΔT of the testing at a same reaction duration is substantially reduced. Therefore, disadvantages of scale-forming and over oxidization caused by increasing the reaction time can be avoided.

Figure 3:
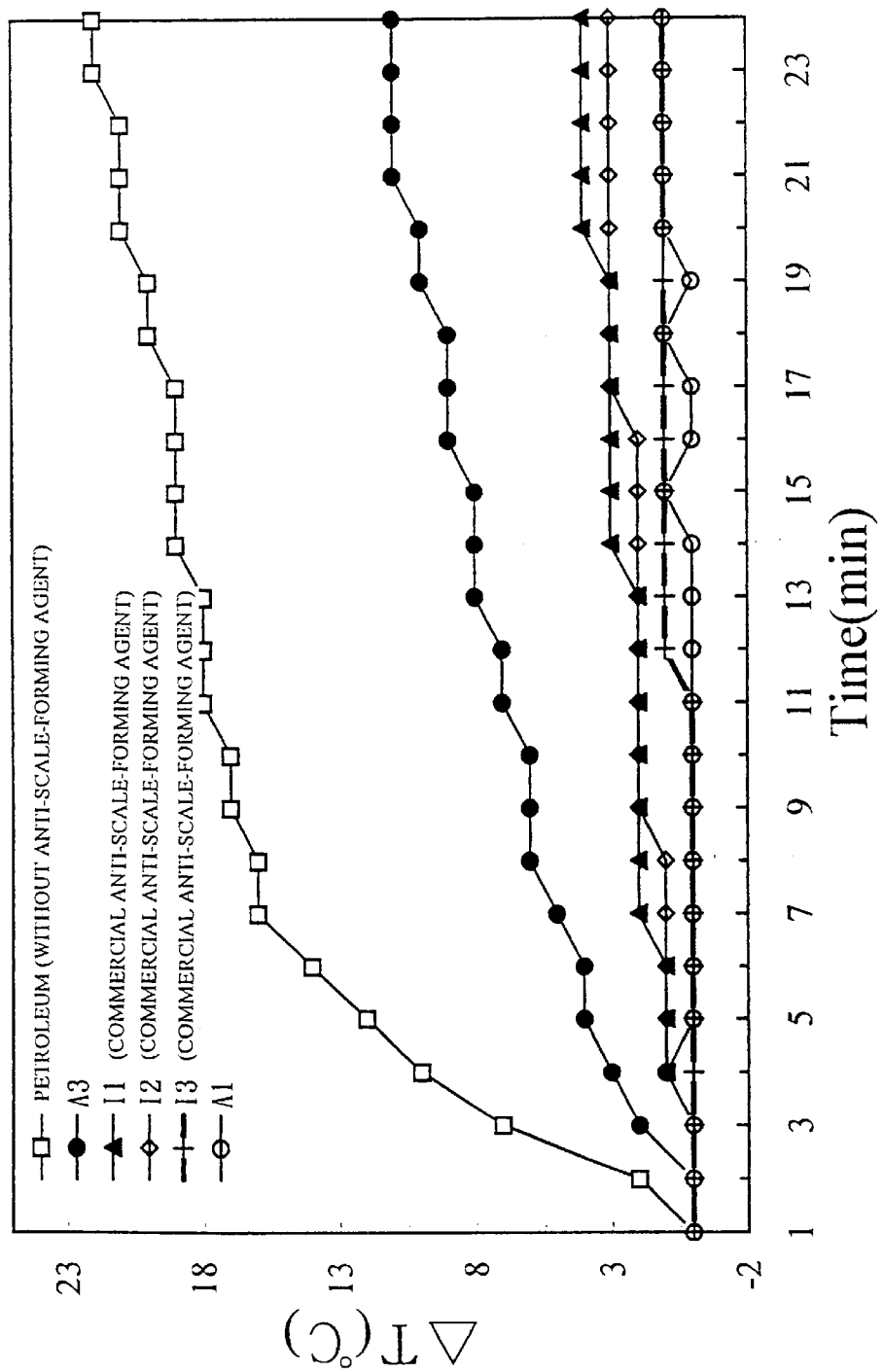
FIG. 3 is a comparison of some ASTM D3241 testing results by respectively adding the anti-scale-forming agent of the present invention and some commercial anti-scale-forming agents into the oil.

FIG. 3 is a comparison of some ASTM D3241 testing results by respectively adding the anti-scale-forming agent of the present invention and some commercial anti-scale-forming agents into the oil. The testing pressure and temperature are 500 psi and 371° C., respectively. The 150-ppm anti-oxidization agent is added by a flow rate of 1.5 cc/min. From FIG. 3, it is found that the anti-scale-forming agent A3 of the present invention can reduce the ΔT of the oil having no anti-scale-forming agent added. However, the anti-scale-forming agent A3 of the present invention has obviously not achieved a commercial scale. On the other hand, the anti-scale-forming agent A1 of the present invention does have achieved the commercial scale or a better scale.

The anti-oxidization agent of the present invention, dependent upon the processes and the equipment for use, can be variously and optimally composed to have improved temperature-controllability and the anti-oxidization for being applied to a heat exchanger, a reactor, a distillation tower or the like in a power plant, a refinery factory or the like chemistry factory.

While the present invention has been particularly shown and described with reference to a preferred embodiment, it will be understood by those skilled in the art that various changes in form and detail may be without departing from the spirit and scope of the present invention.

TABLE 1

| SPECIMEN | REACTOR | WEIGHT RATIO | MOLE RATIO | CONDITION | THEORETICAL AMINO TITRATION VALUE | TOTAL AMINE |
|---|---|---|---|---|---|---|
| A1 | PIB-SA/B1 {POCl₃/D-230 (1:3)} | 11.02:4.92 | 1.5:1.0 | 80° C. 3 hr | 1.34 | 0.56 |
| A2 | PIB-SA/B2 {DCP/D-230 (1:4)} | 4.24:3.36 | 1.5:1.0 | 80° C. 3 hr | 1.07 | 0.114 |
| A3 | PIB-SA/B3 {POCl₃/Phenylene diamine (1:3)} | 3.09:0.69 | 1.5:1.0 | 80° C. 3 hr | — | — |
| A4 | PIB-SA/B4 {DCP/Phenylene diamine (1:4)} | 0.72:0.50 | 1.5:1.0 | 80° C. 3 hr | — | — |

| SPECIMEN | 1ˢᵀ DEGREE AMINE | 2ᴺᴰ DEGREE AMINE | 3ᴿᴰ DEGREE AMINE | COLOR | ASTM TESTING | NOTES |
|---|---|---|---|---|---|---|
| A1 | 0.51 | 0.05 | 0 | Transparent Orange | 1° C. low | 1R |
| A2 | 0.114 | 0.05 | 0 | Transparent Orange | | 1R |
| A3 | — | — | — | Dark Green | 22° C. low | 1R |
| A4 | — | — | — | Dark Green Sticky | | 1R |

What is claimed is:

1. An anti-scale forming composition containing an anti-scale-forming agent having a formula:

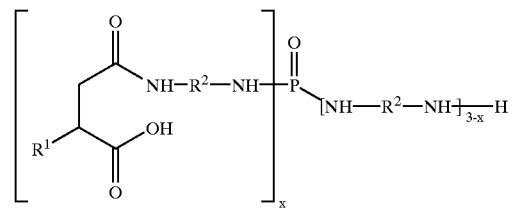

wherein $R^1$ is a polyalkylene group, and $R^2$ is a polyether or a polyoxyalkylene, and x is 1 or 2.

2. The composition according to claim 1, wherein $R^1$ is polyisobutylene and $R^2$ is polyoxypropylene.

3. The composition according to claim 1, wherein the composition has dispersivity and an anti-oxidization properties in accordance with ASTM D3241 testing.

4. The composition according to claim 1, wherein the polyalkylene has a molecular weight of from 600 to 1500.

5. The composition according to claim 1, having a formula

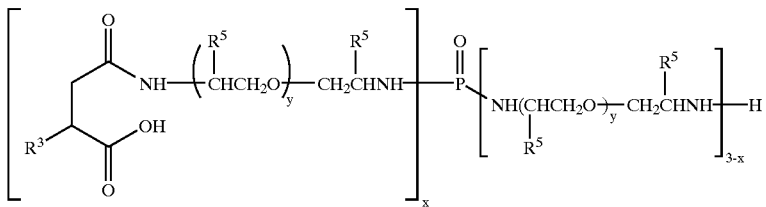

in which R³ is polyisobutylene, R⁵ is hydrogen, methyl or ethyl, and y is an integer ranging from 1 to 20.

6. A composition according to claim 1, wherein the amine portion of the polyether or polyoxyalkylene of the formula is derived from:

$H_2NCH(CH_3)CH_2(OCH_2C(CH_3)H)_xNH_2$ (x=2~3), or $H_2N(CH_2CH_2O)_2CH_2CH_2NH_2$.

7. An anti-scale forming composition containing an anti-scale-forming agent having a formula:

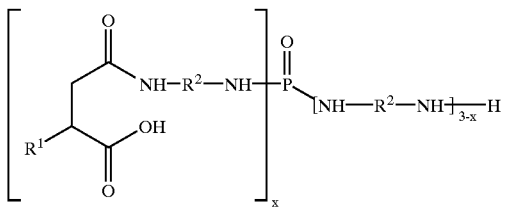

wherein $R^1$ is a polyalkylene group, the amine portion, —NH—$R^2$—NH—, of said formula is derived from:

$H_2NCH_2CH_2NH_2$ (ethylene diarnine, EDA), $H_2N(CH_2)_5NH_2$ (1,6-diamine hexane), $H_2N(CH_2)_2NH(CH_2)_2NH_2$ (diethylene triamine, DETA), $H_2N(CH_2)_2NH(CH_2)_2NH(CH_2)_2NH_2$ (triethylenetetramine, TETA), $(CH_3CH_2)_2N(CH_2)_3NH_2$ (N, N-diethyl-1,3-propane diamine), or $(CH_3)_2N(CH_2)_3NH_2$ (N, N-dimelthyl-1,3-propane diamine); and x is 1 or 2.

* * * * *